United States Patent [19]

Best

[11] Patent Number: 4,612,919
[45] Date of Patent: Sep. 23, 1986

[54] ADJUSTABLE LIMB SUPPORT

[76] Inventor: Walter E. Best, 8111 Bayberry Ct., Indianapolis, Ind. 46250

[21] Appl. No.: 657,132

[22] Filed: Oct. 3, 1984

[51] Int. Cl.⁴ ............................................. A61F 5/00
[52] U.S. Cl. .................................. 128/77; 128/80 F; 128/88
[58] Field of Search ................. 128/80 R, 80 C, 80 F, 128/88, 68, 77, 80 G

[56] References Cited

U.S. PATENT DOCUMENTS

| | | | |
|---|---|---|---|
| 58,403 | 10/1866 | Goodwin | 128/88 |
| 505,382 | 9/1893 | Berghoff | 128/88 |
| 1,340,630 | 5/1920 | Maddox | 128/88 |
| 1,374,177 | 4/1921 | Barry | 128/88 |
| 1,590,499 | 6/1926 | Cozad | 128/80 C |
| 1,643,850 | 9/1927 | Jones | 128/88 |
| 2,832,334 | 4/1958 | Whitelaw | 128/25 |

FOREIGN PATENT DOCUMENTS

| | | | |
|---|---|---|---|
| 11782 | 5/1903 | Austria | 128/25 R |
| 308886 | 11/1918 | Fed. Rep. of Germany | 128/25 R |

Primary Examiner—Clifford D. Crowder
Attorney, Agent, or Firm—Barnes & Thornburg

[57] ABSTRACT

An apparatus is provided for adjustably orienting the forearm and upper arm of a human patient in a variety of angular relationships to therapeutically treat the contracted muscles in the patient's arm. The apparatus includes an exoskeletal frame having a rearward frame member and a forward frame member. The apparatus includes first, second, and third receptacle means pivotally mounted on the frame for positioning the arm in a selected therapeutic position, and orientation means for adjusting the angular displacement between the forward and rearward frame members to progressively and incrementally transport the arm among a variety of therapeutic positions. The first receptacle means includes a pair of cradles which cooperate to embrace the underside of the patient's elbow. The second receptacle means includes a forward saddle for embracing the topside of the patient's forearm. The third receptacle means includes a rearward saddle for embracing the topside of the patient's upper arm. The receptacle means cooperate through the exoskeletal frame to position the articulated human arm in a selected therapeutic arrrangement.

14 Claims, 4 Drawing Figures

ADJUSTABLE LIMB SUPPORT

The present invention relates to a musculoskeletal apparatus for therapeutically treating contracted muscles in an injured human arm. More particularly, the present invention relates to an apparatus for receiving and adjustably orienting an articulated human limb to cause a static load to be applied to certain of the muscles in the human limb to therapeutically exercise or otherwise treat the limb.

Muscle contracture of a human limb such as an arm is a serious problem. Various muscles in the human arm can become contracted due to trauma suffered during a serious accident such as automobile accident. For example, a serious head or spinal-cord injury can block motor impulse signals from the brain to cause the muscles in the arm to contract. Complications, such as myositis ossificians, after an injury can partially cause muscle contracture. The foregoing maladies often cause a patient's biceps to contract thereby drawing the forearm of the injured patient toward the patient's chest in proximity to the collarbone.

Physiotherapy is often prescribed to exercise the contracted muscles in the injured arm. One aspect of this treatment includes the manual manipulation of the injured arm by a trained physiotherapist. Another aspect of this treatment requires the patient's injured arm to be placed in a variety of differently shaped casts over a long period of time in an effort to progressively unfold the patient's injured arm from the above-described contracted position to its normal fully-extended position.

A typical rehabilitation schedule includes a periodic, often weekly, session with a physiotherapist. At the conclusion of such a session, a conventional plaster cast is usually applied to the arm to incrementally move the inwardly drawn forearm to a more fully-extended position.

Initially, when the injured forearm is drawn inwardly toward the patient's chest, the injured forearm and the injured upper arm cooperate to define an acute angle. The object of the series of casts is to progressively and regularly increase the angular displacement between the debilitated upper arm and forearm until the entire arm is extendable by the patient to a fully extended position.

The theory behind serial casting is that the tendons and muscles will be stretched while being held for a week in a fixed position. Then, apply a new cast with the arm now extended to a greater angle so that with each casting, the angle of the arm is slowly extended until it is stretched. This method, however, does nothing to strengthen the triceps. So, upon completion of the serial casting, the muscles and tendons have been stretched so that a full range of motion is possible. The theory of the present invention is to use this device to extend the arm gradually as the muscles are stretched and to allow some therapy (to incite action with the triceps) at regular short intervals. This device is to be used during times of relaxation to hold the arm in the furthest extension possible without pain but to permit therapy at any time. At each step of serial casting, the old plaster cast is removed and a fresh, new plaster cast is applied. This static load causes the muscles in the arm to be stretched during the period of time between physical therapy sessions.

Conventional plaster casts do not perform or wear well when used during this type of treatment for a variety of reasons. It will be understood that a patient's inner forearm is generally bruised and made tender due to abrasive contact with the inner wall of the conventional plaster cast. The tightened, paralyzed muscles in the patient's arm cause the arm to behave like a "leaf" spring. Thus, the muscles exert a force to urge the inner surface of the patient's forearm into painful engagement with the inner wall of the plaster cast. Any failure of the conventional cast exacerbates the patient's arm injury. A conventional plaster cast does not adequately support the inwardly drawn, injured limb along the entire length of the stationary cast. It will also be appreciated that plaster casts are, as a general rule, uncomfortable and obtrusive. Daily showering and maintenance of personal hygiene is very difficult for one sentenced to wear a great number and variety of casts for a long period of time. Notwithstanding the comfort problem, it is also costly, time consuming, and otherwise inconvenient to have a new plaster cast applied every week or so. This is especially true for a patient who sustained many other serious injuries during the same accident in which the patient received the arm injury.

A removable and reusable limb support designed to receive and adjustably orient the forearm and upper arm of a patient in a variety of angular relationships to therapeutically treat the contracted muscles in the arm would avoid the shortcomings of conventional plaster casts.

According to the present invention, an apparatus for adjustably orienting the forearm and upper arm of a traumatized human arm comprises an exoskeletal frame including a rearward frame member and a forward frame member, first, second, and third receptacle means pivotally mounted on the frame for positioning the arm in a selected therapeutic position, and orientation means for adjusting the angular displacement between the forward and rearward frame members to progressively and incrementally transport the arm among a variety of therapeutic positions.

The first receptacle means includes a pair of cradles which cooperate to embrace the underside of the patient's elbow. The second receptacle means includes a forward saddle for embracing the topside of the patient's forearm. The third receptacle means includes a rearward saddle for embracing the topside of the patient's upper arm. The receptacle means cooperate through the exoskeletal frame to position the articulated human arm in a selected therapeutic arrangement.

One feature of the present invention is the provision of a lightweight, exoskeletal frame for orienting an articulated human limb such as an arm. The frame is easily fitted on a patient's injured arm in only a few moments with a minimum of effort. Further, the apparatus is easily removed at various times during the day. Removal of the apparatus enables the injured patient to shower without taking the extreme precautions that must generally taken to protect a conventional plaster cast. A family member or companion of the injured patient can be quickly trained to install and remove the novel frame assembly thus avoiding the great cost and inconvenience of traveling to an orthopedic technician skilled in the practice of making plaster casts.

Another feature of the present invention is the provision of three spaced-apart receptacle means on the frame for positioning the articulated limb in a therapeutic position. The receptacle means cooperate to support the limb at at least three points along its length. Thus, the force exerted by the triceps and other muscles in the inwardly drawn injured arm is distributed over the entire length of the patient's arm rather than being applied to a small area on the patient's forearm as is the case in a plaster cast. Thus, the novel receptacle means advantageously minimizes further bruising and damage to an already injured arm.

Yet another feature is the provision of a first receptacle means including forward and rearward cradles for carrying and supporting the articulated limb, the cradles being pivotally mounted on a plate which is pivotally mounted on a frame member. This feature advantageously allows the patient or another to pivotally adjust the position of the forward and rearward cradle about the patient's elbow independent of the relative position of the forward and rearward frame members. Thus, it is still possible to adjust the cradles to provide maximum elbow support and comfort after the patient's upper arm and forearm are restrained by the exoskeletal frame in the relative angular position that is appropriate to that particular stage of the patient's progressive rehabilitation.

Still another feature of the present invention is the provision of orientation means for adjusting the angular displacement between the limb-carrying forward and rearward frame members. Such a feature advantageously enables the patient or another to therapeutically treat certain muscles in one or both of the forearm and upper arm by causing the forearm to rotate or unfold in relation to the upper arm from an inwardly-drawn position to a more fully extended position. The angular displacement between the forearm and the upper arm can be incrementally varied, thus avoiding the present need to apply and remove a great number of conventional plaster casts. The present apparatus is easily adjustable to provide an exact angular relationship. An angular scale can be inscribed on the frame to enable a user to repeatedly obtain an accurate measure of the angular displacement between the forward and rearward frame members. Thus, the required angular relationship between forward and rearward frame members can always be easily obtained even if the frame is removed and reinstalled on several occasions during the patient3 s daily routine.

Additional features and advantages of the invention will become apparent to those skilled in the art upon consideration of the following detailed description of a preferred embodiment exemplifying the best mode of carrying out the invention as presently perceived. The detailed description particularly refers to the accompanying figures in which.

Figure 1:
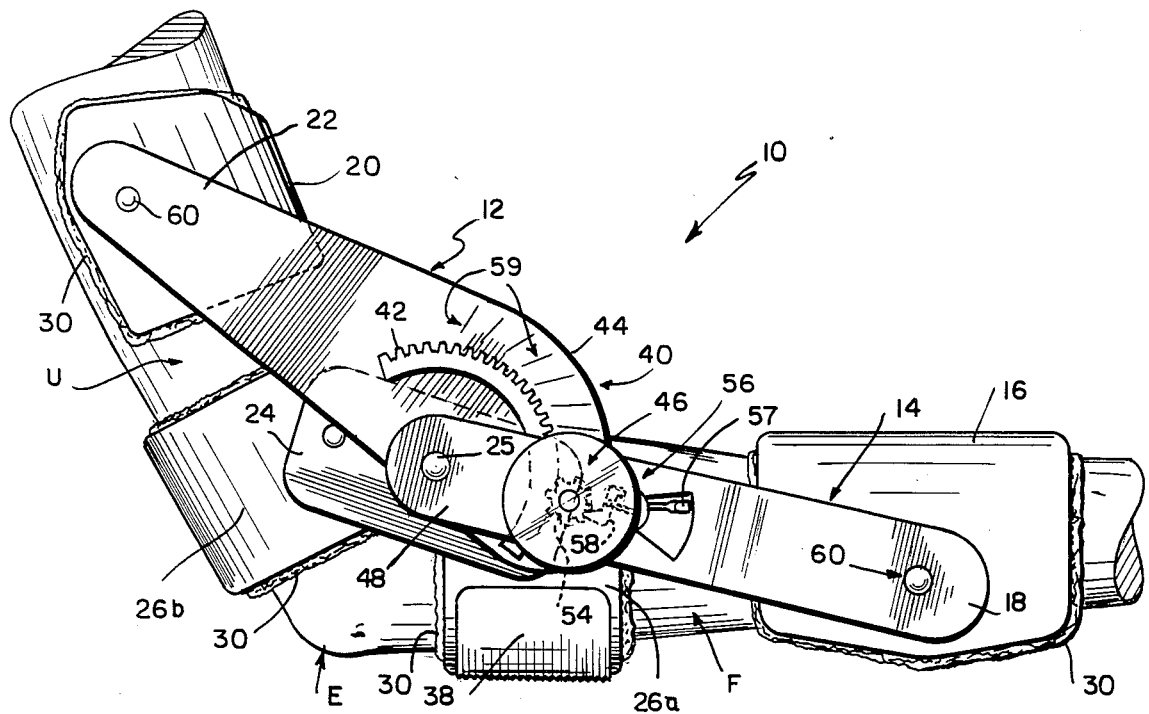
FIG. 1 is a side elevation view of an adjustable limb support embodying the present invention shown in an operative position on a human right arm.

An adjustable limb support apparatus 10 of the present invention is shown in an operative position on a patient's right arm in FIG. 1. The apparatus 10 includes a rearward frame member 12 and a forward frame member 14 pivotally mounted on the rearward frame member 12 to form an articulated linkage. The frame members 12, 14 having sufficient strength and low weight can be constructed of aluminum having a thickness of three-sixteenths of an inch.

A forward saddle 16 is pivotally mounted on the distal end 18 of the forward frame member 14 to receive and embrace the patient's forearm (F). A rearward saddle 20 is pivotally mounted on the distal end 22 of the rearward frame member 12 to engage the patient's upper arm (U). An elongated plate 24 is pivotally mounted on the rearward frame member 12 so that the plate 24 and the forward frame member 14 are coaxially aligned to pivot about the same axis defined by pivot pin 25. A pair of cradles 26a and 26b are pivotally mounted at opposite ends of plate 24 to provide a means for embracing the articulated limb in close proximity to the elbow joint (E) uniting the forearm (F) and upper arm (U).

Figure 2:
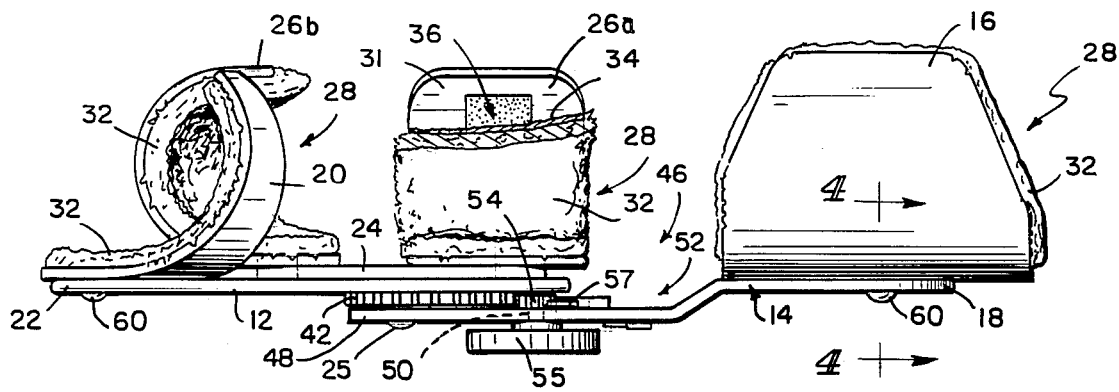
FIG. 2 is a top plan view of the invention in FIG. 1 with portions broken away and the human arm removed therefrom.
Figure 3:
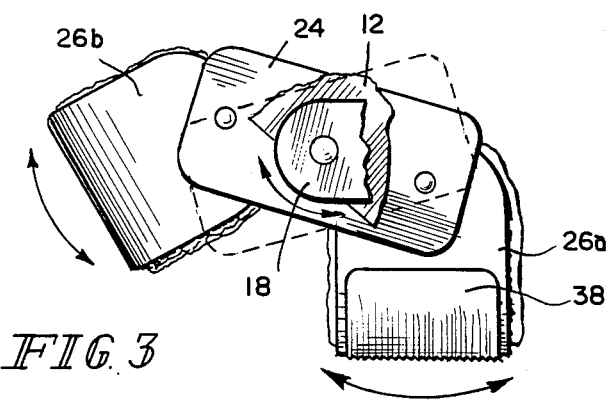
FIG. 3 is an enlarged view of the first receptacle means of the present invention showing the pivotal movement thereof with portions broken away.

Each of the saddles 16, 20 and the cradles 26a, 26b are elongated shells that are substantially C-shaped in transverse cross section to provide a cylindrically, concave surface 28 for receiving a portion of the patient's arm therein. Thus, the saddles and cradles are shaped and positioned to distribute the force exerted by the inwardly-drawn forearm (F) along substantially the entire length of the patient's arm. Soft pads 30 are mounted on the arcuate inner surface 31 of each of the saddles and cradles to provide comfort to the patient. Soft pads 30 may be a composite assembly including a cushion layer 32 of synthetic lambskin or the like having a backing 34 of dense long pile carpet or the like as shown best in FIG. 2. In addition, VELCRO strips 36 or the like can be attached to the pad backing 34 and also to the arcuate inner surface 31 of each of the saddles and cradles to enable a user to easily remove the soft pads 30 for cleaning. Saddles and cradles of sufficient strength and low weight can be constructed of aluminum having a thickness of one-eighth inch. Desirably, the forwardmost cradle 26a is provided with a "non-skid" friction grip 38 fastened to its outer surface. The friction grip 38 may be constructed of rubber or any suitable synthetic material. The friction grip 38 is located to contact the arm of a wheelchair (not shown) in which the patient may be seated to help prevent slippage of the arm-carrying frame assembly 10 on the wheelchair arm.

The apparatus further includes orientation means 40 for adjusting the angular displacement between the forward and rearward frame members 14, 12. The orientation means includes a semicircular drive rack 42 mounted on the proximal end 44 of the rearward frame member 12, and a pinion assembly 46 mounted on the proximal end 48 of the forward frame member 14. The pinion assembly 46 includes a shaft 50 extending through an aperture 52 formed in proximal end 48 and rotatable therein, a pinion 54 rigidly fixed to one end of the shaft 50 to engage the drive rack 42, and a turn knob 55 rigidly fixed to the other end of shaft 50 to enable a user to operate the rack and pinion assembly 40 to adjust the angular displacement of the frame members 12, 14.

The orientation means 40 further includes a ratchet assembly 56 or any other suitable means for selectively locking the pinion assembly 46 against counterclockwise rotation. The ratchet assembly 56 includes a trigger 57 pivotally mounted on the forward frame member 14 in close proximity to the pinion 54 and a conventional spring-loaded pawl 58 mounted therebetween. The trigger 57 is movable between an operating position (shown in FIG. 1) and a locked position (not shown) to permit the apparatus 10 to be operated.

Figure 4:
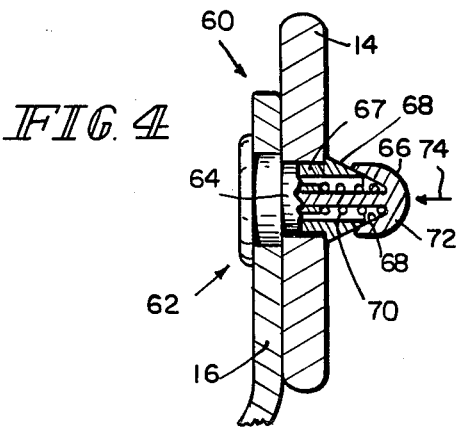
FIG. 4 is an enlarged sectional detail view of the invention taken generally along lines 4—4 of FIG. 2.

The forward and rearward saddles 16, 20 can be detachably mounted to the frame members, 14 and 12 respectively, using the spring-loaded bushing assembly 60 illustrated in FIG. 4 or any other suitable attachment means. Bushing assembly 60 includes a bushing 62 having a resilient annular base 64 and a retaining member 66. The base includes peripheral flanges 67. The base 64 and retaining member 66 each have confronting caming surfaces 68. The retaining member 66 is loaded in its bushing retaining position by spring 70 as shown in FIG. 4. For example, the bushing assembly 60 is operable to detach the saddle 16 by depression of the button head 72 of retaining member 66 in direction 74 to cause the peripheral flanges 67 to be radially inwardly cammed by relative movement of confronting camming surface 68 and disengaged from the forward frame member 14.

The adjustable limb support of the present invention is operable in the following manner to therapeutically treat an injured arm. The apparatus 10 is operable to move or unfold the patient's forearm (F) from an inwardly-drawn position to a more fully-extended position in opposition to the constant inward force exerted by the biceps in the patient's upper arm (U). The biceps will continue to exert such an inward force until the patient's arm injury has been remedied. The trigger 57 is moved to its operating position shown in FIG. 1 to "unlock" the forward frame member 14. The forward frame member 14 is free to move in a counterclockwise direction toward the rearward frame member 12 in response to the inward force exerted by the patient's arm. Operation of trigger 57 enables the user to use turnknob 55 to incrementally rotate the forward frame member 14 in a clockwise direction in opposition to the inward force exerted by the patient's triceps. It will be appreciated that the interplay and constant tension between the patient's inwardly drawn arm and the "locked" frame assembly 10 cooperate to retain the apparatus 10 on the patient's arm. The turn knob 55 should be rotated in a clockwise direction to cause the pinion 57 to navigate the drive rack 42 and to cause the patient's forearm (F) to be pivotally moved with respect to the patient's upper arm (U) about the elbow joint (E) and thus increase the angular displacement between the frame members 12 and 14. The graduated scale 59 can be used to assist the user in measuring the angular displacement between the patients forearm (F) and upper arm (U).

Each of the articulated limb portions is laterally and longitudinally movable to a small degree within the constraints of the exoskeletal frame 10 due to the structure of saddles 16, 20 and cradles 26a,b even when the articulated limb is positioned in the selected therapeutic position. Such slight movement is possible since the apparatus 10 is held in place on the patient's arm by the inwardly directed forces exerted by the arm muscles on the saddles and cradles and not by any affirmative gripping action or the like.

The apparatus 10 is operable to return the forearm to an inwardly-drawn position by moving the trigger 57 to a ratchet-disabling position (not shown) to permit the forward frame member 14 to be freely rotatable along drive rack 42 in either direction. It will be understood that turn-knob 55 will automatically rotate in the chosen direction simultaneous with movement of the forward frame member 14.

In one embodiment of the present invention, the semicircular drive rack 42 is replaced with a substantially circular drive rack (not shown). Such a feature permits the forward frame member 19 to be fully mobile about pivot 25 with respect to the rearward frame member 12 so that the limb support of the present invention could be used on either a left arm or a right arm.

Although the invention has been described in detail with reference to certain preferred embodiments and specific examples, variations and modifications exist within the scope and spirit of the invention as described and defined in the following claims.

What is claimed is:

1. An apparatus for adjustably orienting an articulated human limb of a patient in a plurality of therapeutic positions, the human limb having an upper portion and a lower portion, the apparatus comprising a frame including a rearward frame member and a forward frame member, the forward frame member being mounted for pivotal movement on the rearward frame member, first receptacle means for embracing at least one of the articulated limb portions in close proximity to a joint uniting the articulated limb portions, the first receptacle means being mounted on the frame for pivotal movement about a transverse axis orthogonal to the frame, second receptacle means for embracing one of the upper portion and the lower portion of the articulated limb, the second receptacle means being mounted on the forward frame member for pivotal movement about a second transverse axis orthogonal to the frame, third receptacle means for embracing the other of the upper portion and the lower portion of the articulated limb, the third receptacle means being mounted on the rearward frame member for pivotal movement about a third transverse axis orthogonal to the frame, and orientation means for adjusting the angular displacement between the forward and rearward frame members to pivot the first, second, and third receptacle means about their respective transverse axes to position the limb received within the first, second, and third receptacle means and therapeutically treat certain muscles in one or both of the articulated human limb portions by causing one of the articulated limb portions received in its companion receptacle means to rotate in relation to the other limb portion received in its companion receptacle means through a selected angle.

2. The apparatus of claim 1 wherein the first receptacle means includes a plate journaled for pivotal movement to the rearward frame member, and forward and rearward cradles for carrying and supporting the articulated human limb, the forward cradle being journaled for pivotal movement to one end of the plate to receive and embrace one of the articulated human limb portions, and the rearward cradle being journaled for pivotal movement to the other end of the plate to receive and embrace the other of the articulated human limb portions such that the position of the forward and rearward cradles relative to the adjacent frame is adjustable or otherwise variable independent of the relative position of the forward and rearward frame members to manipulate the position of at least one of the articulated human limb portions in close proximity to a joint uniting the articulated limb to provide therapeutic support thereto.

3. The apparatus of claim 1 wherein the second receptacle means includes a forward saddle for manipulating the position of the lower limb portion, the forward saddle being journaled for pivotal movement to the forward frame member to receive and embrace the lower limb portion, and the third receptacle means includes a rearward saddle for manipulating the position of the upper limb portion, the rearward saddle being journaled for pivotal movement to the rearward frame member to receive and embrace the upper limb portion.

4. The apparatus of claim 1 wherein the orientation means includes a drive rack rigidly fixed to the proximal end of the rearward frame member in close proximity to the joint uniting the pivotally coupled frame members, and pinion means, rotatably mounted to the proximal end of the forward frame member in close proximity to the drive rack on the rearward frame member, for navigating the drive rack to cause the forward frame member to rotate through a selected angle in response to rotation of the pinion means.

5. The apparatus of claim 4 wherein the pinion means includes a shaft extending through an aperture formed in the proximal end of the forward frame member and rotatable therein, a pinion rigidly fixed to one end of the shaft to engage the drive rack, and a turn knob rigidly fixed to the other end of the shaft to enable a user to operate the apparatus.

6. An apparatus for embracing the top side and bottom side of a human arm in a plurality of therapeutic positions, the apparatus comprising a frame including a rearward frame member and a forward frame member, the forward frame member being pivotally mounted on the rearward frame member, first means, on the rearward frame member, for embracing the top side of the human upper arm, second means for embracing the bottom side of the human upper arm and forearm, the second means including a plate journaled for pivotal movement to at least one of the frame members, a forward cradle, and a rearward cradle, the forward and rearward cradles each being attached to the plate and cooperating to support simultaneously both of the human upper arm and forearm in close proximity to the elbow of the human arm, third means, on the forward frame member, for embracing the top side of the human forearm, and orientation means, on the forward and rearward frame members, for pivoting the forward frame member in relation to the rearward frame member to straighten an otherwise bent human arm.

7. An apparatus for adjustably orienting an articulated human limb of a patient in a plurality of therapeutic positions, the human limb having an upper portion and a lower portion, the apparatus comprising a frame including a rearward frame member and a forward frame member, the forward frame member being pivotally connected to the rearward frame member, first receptacle means pivotally mounted on the frame for embracing at least one of the articulated limb portions in close proximity to a joint uniting the articulated limb portions, the first receptacle means including a plate journaled for pivotal movement to the frame, and forward and rearward cradles for carrying and supporting the articulated human limb, the forward cradle being journaled for pivotal movement to one end of the plate to receive and embrace one of the articulated human limb portions, and the rearward cradle being journaled for pivotal movement to the other end of the plate to receive and embrace the other of the articulated human limb portions such that the position of the forward and rearward cradles relative to the adjacent frame is adjustable or otherwise variable independent of the relative position of the forward and rearward frame members to manipulate the position of at least one of the articulated human limb portions in close proximity to a joint uniting the articulated limb to provide therapeutic support thereto, second receptacle means for embracing one of the upper portion and the lower portion of the articulated limb, the second receptacle means being pivotally mounted on the forward frame member, third receptacle means for embracing the other of the upper portion and the lower portion of the articulated limb, the third receptacle means being pivotally mounted on the rearward frame member, and orientation means for adjusting the angular displacement between the forward and rearward frame members to position the limb received within the first, second, and third receptacle means and treat certain muscles in one or both of the articulated human limb portions therapeutically by causing one of the received articulated limb portions to rotate in relation to the other received limb portion through a selected angle.

8. The apparatus of claim 7, wherein the second receptacle means includes a forward saddle for maipulating the postion of the lower limb portion, the forward saddle being journaled for pivotal movement ot the forward frame member to receive and embrace the lower limb portion, and the third receptacle means includes a rearward saddle for manipulating the position of the upper limb portion, the rearward saddle being journaled for pivotal movement to the rearward frame member to receive and embrace the upper limb portion.

9. The apparatus of claim 7, wherein the orientation means includes a drive rack rigidly fixed to the proximal end of the rearward frame member in close proximity to the joint uniting the pivotally coupled frame members, and pinion means, rotatably mounted to the proximal end of the forward frame member in close proximity to the drive rack on the rearward frame member, for navigating the drive rack to cause the forward frame member to rotate through a selected angle in response to rotation of the pinion means.

10. The apparatus of claim 9, wherein the pinion means includes a shaft extending through an aperture formed in the proximal end of the forward frame member and rotatable therein, a pinion rigidly fixed to one end of the shaft to engage the drive rack, and a turn knob rigidly fixed to the other end of the shaft to enable a user to operate the apparatus.

11. An apparatus for adjustably orienting an articulated human limb of a patient in a plurality of therapeutic positions, the limb having an upper portion and a lower portion, each portion having an underside and a topside region, the apparatus comprising first receptacle means for simultaneously embracing only the underside region of both of the articulated limb portions in close proximity to an elbow joint uniting the articulated limb portions, second receptacle means for embracing only the topside region of the upper portion to compress the upper portion between the first and second receptacle means, third receptacle means for embracing only the topside region of the lower portion to compress the lower portion between the second and third receptacle means, and orientation means for adjusting the angular displacement between the second receptacle means and the first and third receptacle means to position the upper and lower portions of the limb received within the first, second, and third receptacle means, the orientation means being configured to support the first, second, and third receptacle means sequentially in mutually space-apart relation to clamp the articulated human limb of the patient in a three-point gripping arrangement, the space-apart first and second receptacle means cooperating to induce rotation of the upper portion of the articulated human limb in a counterclockwise direction and the space-apart second and third receptacle means cooperating to induce rotation of the lower portion of the articulated human limb in a clockwise direction in response to operation of the orientation means so that the orientation means therapeutically treats certain muscles in one or both of the articulated human limb portions by causing the upper limb portion to rotate in leveraged relation to the lower limb portion through a selected angle while each of the upper and lower portions is held in compression.

12. The apparatus of claim 11, wherein the orientation means includes a rearward frame member and a forward frame member pivotally coupled to the rearward frame member, and the second receptacle means includes a forward saddle for manipulating the position of the lower limb portion, the forward saddle being journaled for pivotal movement to the forward frame member to receive and embrace the lower limb portion, and the third receptacle means includes a rearward saddle for manipulating the position of the upper limb portion, the rearward saddle being journaled for pivotal movement to the rearward frame member to receive and embrace the upper limb portion.

13. The apparatus of claim 11, wherein the orientation means includes a frame including a rearward frame member and a forward frame member pivotally coupled to the rearward frame member, a drive rack rigidly fixed to the proximal end of the rearward frame member in close proximity to the joint uniting the pivotally coupled frame members, and pinion means, rotatably mounted to the proximal end of the forward frame member in close proximity to the drive rack on the rearward frame member, for navigating the drive rack to cause the forward frame member to rotate through a selected angle in response to rotation of the pinion means.

14. The apparatus of claim 13 wherein the pinion means includes a shaft extending through an aperture formed in the proximal end of the forward frame member and rotatable therein, a pinion rigidly fixed to one end of the shaft to engage the drive rack, and a turn knob rigidly fixed to the other end of the shaft to enable a user to operate the apparatus.

* * * * *